(12) United States Patent
Garcia et al.

(10) Patent No.: US 6,598,808 B1
(45) Date of Patent: Jul. 29, 2003

(54) FLUID PRODUCT SAMPLE

(75) Inventors: Firmin Garcia, Evreux (FR); Aline Abergel, Boulogne Billancourt (FR)

(73) Assignee: Valois S.A., Le Neubourg (FR)

( * ) Notice: Subject to any disclaimer, the term of this patent is extended or adjusted under 35 U.S.C. 154(b) by 0 days.

(21) Appl. No.: 09/744,714

(22) PCT Filed: Jul. 28, 1999

(86) PCT No.: PCT/FR99/01853

§ 371 (c)(1),
(2), (4) Date: Apr. 3, 2001

(87) PCT Pub. No.: WO00/06464

PCT Pub. Date: Feb. 10, 2000

(30) Foreign Application Priority Data

Jul. 30, 1998 (FR) .............................. 98 09746

(51) Int. Cl.[7] .............................. B65D 1/32; B05B 9/00
(52) U.S. Cl. .................. 239/327; 239/309; 239/326; 239/596; 239/600; 222/107; 222/187; 222/215; 222/541.9; 422/120; 422/124; 422/305
(58) Field of Search ................ 239/145, 309, 239/326, 327, 526, 600; 222/107, 187, 215, 541.1, 541.9; 206/461, 462, 471; 422/120, 122, 123, 124, 305, 306

(56) References Cited

U.S. PATENT DOCUMENTS

| 3,412,907 | A | | 11/1968 | Faso | |
|---|---|---|---|---|---|
| 3,913,789 | A | * | 10/1975 | Miller | 222/187 |
| 3,917,116 | A | * | 11/1975 | Mason | 222/187 |
| 4,858,831 | A | | 8/1989 | Spector | |
| 4,869,407 | A | * | 9/1989 | Booth et al. | 206/461 |
| 5,388,762 | A | * | 2/1995 | Bryson, Sr. | 239/327 |
| 5,738,831 | A | * | 4/1998 | Bethel | 422/120 |
| 6,254,836 | B1 | * | 7/2001 | Fry | 422/122 |

FOREIGN PATENT DOCUMENTS

| EP | 0 496 460 A | 7/1992 |
|---|---|---|
| GB | 2038757 A | 7/1980 |
| JP | 08040478 A | 2/1996 |
| WO | WO 97 27043 A | 7/1997 |

* cited by examiner

Primary Examiner—Steven J. Ganey
(74) Attorney, Agent, or Firm—Wood, Phillips, Katz, Clark & Mortimer

(57) ABSTRACT

A fluid product sample is provided in the form of a substantially flat dispenser. A preferred embodiment includes (1) at least one thermoformed shell forming part of a reservoir and defining a deformable actuation wall; (2) an additional element, such as a capsule-forming substrate or film or a thermoformed shell for finishing off the reservoir, with the reservoir formed in this way containing at least a gas; (3) a spray orifice through which the fluid is sprayed; (4) a porous material piece which is capable of retaining a quantity of fluid and which is disposed upstream from the spray orifice; and (5) a support member fixed to the thermoformed shell to hold the porous material piece in place. The spray orifice is formed by the support member.

29 Claims, 4 Drawing Sheets

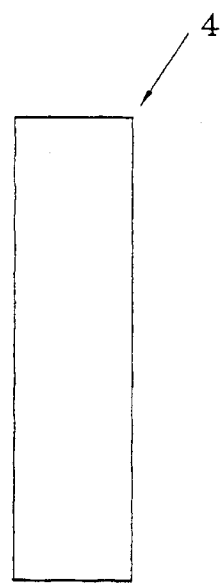
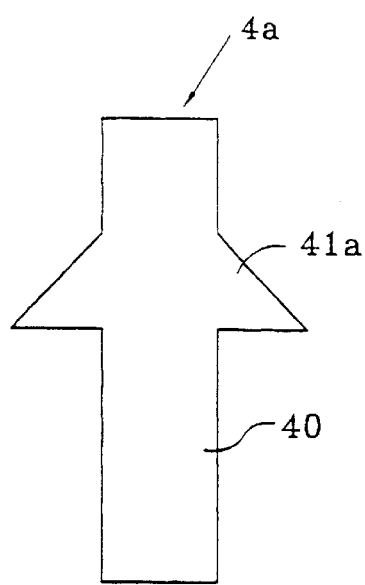
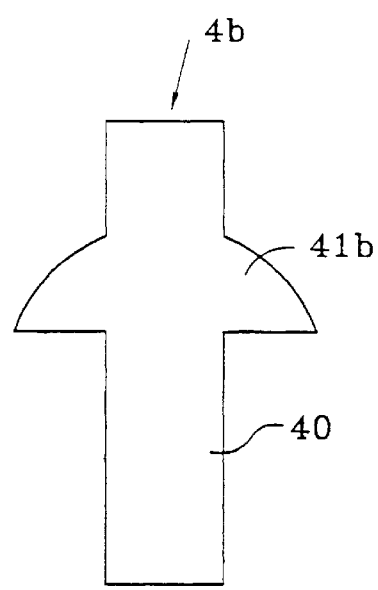
FIG.8　　　FIG.8a　　　FIG.8b
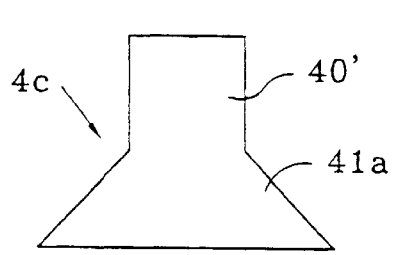
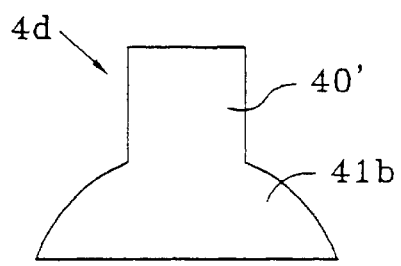
FIG.8c　　　FIG.8d

FLUID PRODUCT SAMPLE

This application is an application filed under 35 U.S.C. Sec. 371 as a national stage of international application PCT/FR99/01853, which was filed Jul. 28, 1999.

The present invention relates to a fluid product sample in the form of a substantially flat dispenser. The invention thus relates to a miniature spray that is preferably discardable and that is adapted in particular to the fields of perfumery or cosmetics.

BACKGROUND OF THE INVENTION

The problems which arise for such a fluid dispenser lie particularly with the requirements for manufacture to be low cost. Since product samples are generally not for sale, manufacturing cost must be as low as possible. It is therefore important to have devices whose parts are easily mass produced and which can be assembled together simply. In addition, since product samples are used mainly for publicity purposes, it is desirable to be able to be place a trademark, logo, or other distinctive sign corresponding to the product contained in the dispenser in visible manner thereon. Similarly, it is desirable to provide a device that is original in shape and practical to use. For example, for product samples that are to be included in magazines and newspapers, it is essential for the dispenser to be very thin. Furthermore, it is also important for spraying to be of good quality.

The dispenser device of the invention can also find applications in the field of pharmacy. In this particular field, it is important for the dose of fluid to be accurate.

By way of example, document FR-A-2 443 980 discloses a discardable spray made by sheets of plastic which are heat-sealed together to define between them a reservoir and two swirling channels connected to a spray orifice. By pressing on the reservoir whose walls are made by the sheets of plastic, fluid is delivered into the swirling channels and then through the spray orifice so as to spray a jet of the product. Nevertheless, that discardable spray is not suitable for expelling a defined dose of the fluid. Furthermore, making swirling channels by heat-sealing two sheets of plastic together is rather inaccurate and random. In one version of that spray, the reservoir is subdivided into two chambers by a partition which breaks under the action of the pressure. One chamber is filled with a fluid while the other chamber contains another fluid and air. In addition, the reservoir is separated from the spray orifice by a weak point. Initially, when pressure is applied to the reservoir, the partition breaks and the two fluids mix together and with the air to a greater or lesser extent. In any event, the mixing performed in this way cannot be homogeneous. By increasing the pressure, the point of weakness is broken and the non-homogeneous mixture is delivered to the spray orifice. The jet leaving the orifice is sometimes made up of the first fluid, sometimes of the second fluid, and sometimes of air, but it is never a homogenous-mixture of all three; As a result the jet is sometimes purely aqueous and sometimes it is made up of two phases. Its quality is therefore not constant.

Document WO 98/01360 discloses a two-phase dispenser capable of delivering a measured quantity of fluid in the form of a spray. That dispenser is also designed to serve as a miniature spray in the form of a product sample. It has two air reservoirs and one reservoir for the fluid, with all of the reservoirs being connected to a common spray orifice. Upstream from the spray orifice, there is provided a fiber which is capable of being soaked in the fluid. Consequently, the air which is expelled from the air reservoir passes through the fiber which is soaked with the fluid that is expelled from the two fluid reservoirs. To actuate the device, a presser member is provided in the form of a tongue that can be applied to the reservoirs in such a manner as to squash them, thereby causing the fluid and the air to be delivered to the spray orifice. The various reservoirs are formed between a support and a flexible barrier film. The presser tongue has the effect of pressing the film against the support where together they form the reservoirs for the fluid and air.

In that dispenser, the fiber which serves as means for retaining the fluid and for passing the air is received in a recess formed by the support film. At the outlet from the fiber, the fluid is merely propelled by the air through the spray orifice which is formed by the film being locally separate. Consequently, the shape of the spray orifice is not suitable for supplying a spray jet of acceptable quality. In addition, given that the fiber is protected only by the film, it can happen that the fiber is damaged through the film. This can cause the fiber to be moved beneath the film which has the effect of spoiling spraying.

Similarly, in the dispenser of document FR-A-2 448 980, the spray orifice is formed in one or the other of the two plastic sheets in the form of a simple hole. As a result, the shape of the orifice is not precise and this affects the quality of spraying.

Mention can also be made of document U.S. Pat. No. 4,858,831 which describes a spray comprising shell closed by a capsule and in which the spray orifice is formed. A porous disk is placed upstream from the orifice and is held in place in a tube which is fixed to the shell. In that case also, the spray orifice formed in the shell cannot be of good quality because of the nature of the shell.

SUMMARY OF THE INVENTION

An object of the present invention is to solve this problem of the prior art by defining a low cost dispenser device which ensures that spraying is of good quality under all circumstances. In addition, the volume of the dose that is delivered should be constant and accurate. Furthermore, in certain applications, and in particular in publicity applications, the dispenser should satisfy certain dimensional requirements, in particular it should be very thin so as to be suitable for being incorporated in a magazine or a journal. It should also be capable of withstanding high pressures without the product leaking out. When such a product sample is included in a journal, for example, and when the journals are stacked, the included product samples are subjected to high pressure.

To resolve this problem, the present invention proposes a fluid product sample in the form of a substantially flat dispenser comprising:

at least one thermoformed shell forming part of a reservoir and defining a deformable actuation wall;

an additional element such as a capsule-forming substrate or film or a thermoformed shell for finishing off the reservoir, with the reservoir formed in this way containing at least a gas;

a spray orifice through which the fluid is sprayed;

a porous material piece capable of retaining a quantity of fluid, said piece being disposed upstream from the spray orifice and placed in contact with and/or soaked in the fluid; and a support member fixed to the thermoformed shell to hold the porous material piece in place, the spray orifice being formed by the support member.

Such a support member thus performs a first function of holding the porous piece, a second function of fixing to the thermoformed shell, and a third function as a surface that defines the spray orifice. In this manner, it is guaranteed that the quality of spraying at the outlet from the spray orifice is good. The porous piece is properly held behind the spray orifice which can be precision-molded in the support member. This is not possible with the dispensers of the two above-mentioned prior art documents since the elements defining the spray orifice cannot be formed with precision given that the first is a flexible barrier film and the second is a flexible plastics sheet. By using a support member that is molded in a plastics material that is relatively hard and having a certain wall thickness, a spray orifice can be molded accurately with a suitable shape, e.g. defining a hole which is extended outwards by a diffusion cone, as is the case for the spray orifice of a conventional spray nozzle.

In an embodiment of the invention, the orifice opens out in the thermoformed shell. In which case the spray orifice can be masked before use by a portion of the thermoformed shell which can be folded back or torn off to unmask the orifice. In a variant, the spray orifice can be masked before use by a tear-off tongue which is stuck to the thermoformed shell. In yet another variant, the support member can form a tear-off endpiece which closes the spray orifice.

In another embodiment, the orifice opens out in the additional element. In this case, the orifice can be masked before use by a tear-off tongue stuck to the additional element.

In yet another embodiment, the support member includes a separate nozzle fitted thereto to define the spray orifice.

Advantageously, the nozzle can be engaged by force in the support member. In addition, the support member can form a tear-off endpiece which closes the spray orifice. Given that the endpiece masks the spray orifice, it is technically easier to form the orifice in a separate element which is substantially mounted on the support member. This simplifies molding and improves precision in the spray orifice.

In order to ensure that the porous piece is properly stable and held well inside the support member, the support member can define a housing in which the piece of porous material is received.

According to another characteristic, the support member defines a shaped appendix for fixing to the thermoformed shell. Advantageously, the shaped appendix has ribs for fixing by heat-sealing.

In another aspect which is particularly advantageous, the support member has a separation wall locally subdividing the reservoir into compartments. In a practical embodiment, the separation wall extends from the appendix, flaring outwardly to form a dome. This separation wall subdividing the reservoir into compartments in the vicinity of the porous piece and thus in the vicinity of the spray orifice has the function of keeping the fluid away from the porous piece while said dispenser is being actuated so that the porous piece presents a maximum surface area for contact with the air present in the reservoir. This ensures proper two-phase dispensing of the fluid. It is important for the porous piece not to be completely immersed during dispensing since that would inevitably give rise to poor quality dispensing due to the absence of the gaseous phase.

Still for the purpose of improving the quality of the two-phase dispensing, the piece made of porous material is of a shape that is suitable for increasing its external surface area so as to increase its contact area with the gas during dispensing. Advantageously, the porous material piece is elongate in shape being placed in the longitudinal direction of the product sample, said piece being formed with a partial collar that defines a substantially semi-annular surface. By increasing the surface area of this porous piece, its contact area with the gas is necessarily increased, thereby increasing the gas content and thus improving the quality of dispensing.

The invention is described more fully below with reference to the accompanying drawings which show various embodiments of the present invention by way of non-limiting example.

BRIEF DESCRIPTION OF THE DRAWINGS

In the drawings:

FIGS. 8 to 8d are cross-sections through pieces made of porous material in a plurality of embodiments;

FIG. 9 is a perspective of a support member in a third embodiment;

FIG. 10a is a view from above of the FIG. 9 support member;

FIG. 10b is a longitudinal section view on line BB of FIG. 10a;

FIG. 10c is a cross-section view on line CC of FIG. 10a;

DETAILED DESCRIPTION OF THE PREFERRED EMBODIMENT

Figure 1:
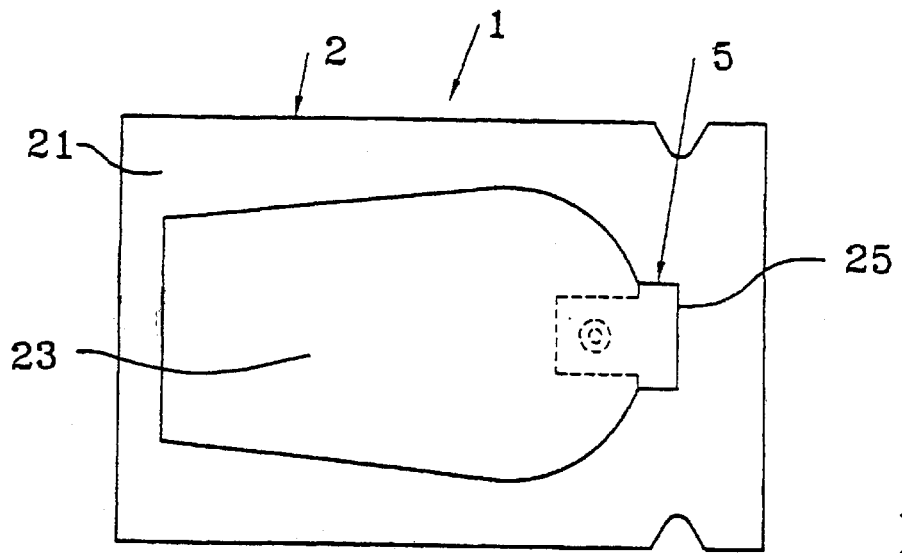
FIG. 1 is a plan view of a product sample constituting a first embodiment of the present invention.
Figure 2:
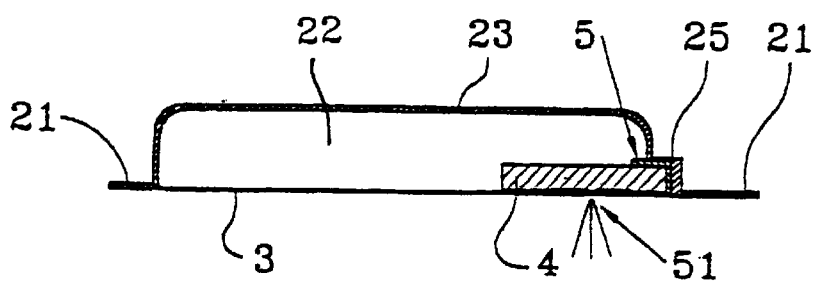
FIG. 2 is a section view of the FIG. 1 product sample.
Figure 3:
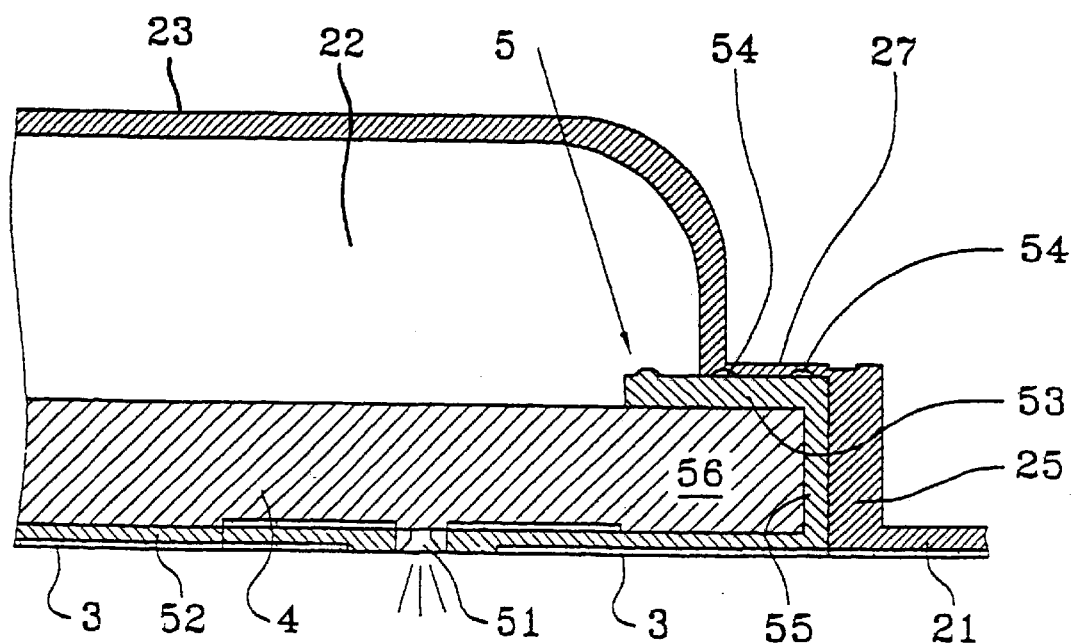
FIG. 3 is a fragmentary view on a much larger scale showing the front portion of the product sample of FIGS. 1 and 2.
Figure 4:
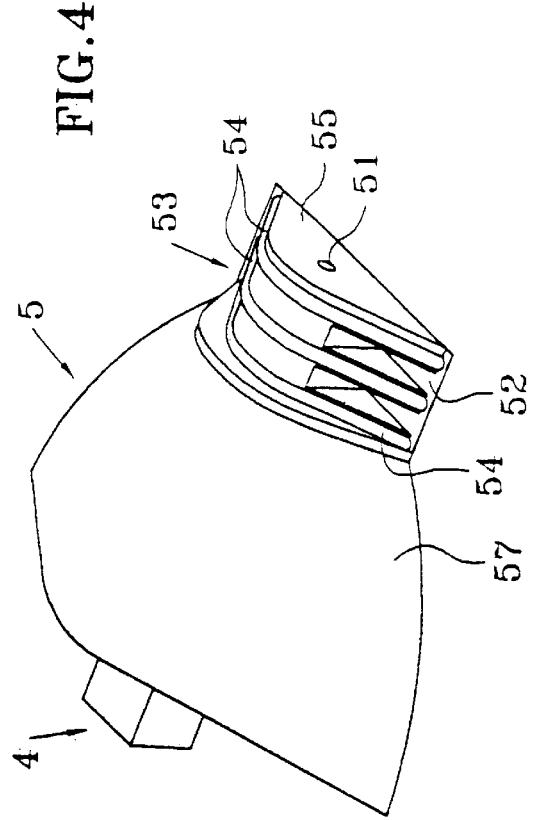
FIG. 4 is a perspective view on a larger scale showing a support member of a second embodiment.

With reference initially to FIGS. 1 to 3, a first embodiment of a fluid product sample of the invention is described. The product sample which is given overall numerical reference 1 essentially comprises four component parts, namely a thermoformed shell 2, an additional element which in this case is in the form of a capsule-forming substrate or film 3, a support member 5, and a piece 4 made of porous material and more clearly visible in FIGS. 2 and 3.

The thermoformed shell 2 comprises a base plane 21 which defines the outside dimensions of the product sample. A convex portion extends from this base plane 21 to form the top wall of a reservoir 22. This convex portion projecting from the base plane 21 thus defines a volume which in the embodiment shown in FIGS. 1 to 3 defines the reservoir 22. To finish off the reservoir, the capsule-forming substrate or film given numerical reference 3 is stuck to the thermoformed shell 2 via its base plane 21. The film can be fixed to the shell 2 by heat-sealing, for example. The film 3 and the shell 2 thus define between them the volume 22 which corresponds to the reservoir. In a variant, it is also possible to replace the capsule-forming film 3 with a second thermoformed shell.

In the invention, the reservoir 22 is filled in part with a fluid while the remaining volume of the reservoir is filled with a gas, e.g. air.

In a variant, the reservoir contains only gas, generally air.

In the invention, the piece of porous material given numerical reference 4 is disposed in the reservoir upstream from a spray orifice 51.

When the reservoir contains fluid, this porous material piece 4 serves to become soaked in the fluid. The porous material piece 4 is thus directly in contact with the fluid and the air inside the reservoir 22.

When the reservoir is filled with air only, the porous material piece is initially soaked in the fluid. Consequently, the porous material piece in this case acts as the reservoir for the fluid, while the air-filled reservoir acts to provide expulsion air.

The product sample 1 is provided with a spray orifice 51 through which the fluid contained in the reservoir 22 or the porous material piece is dispensed in the form of a jet of sprayed fluid. To facilitate such dispensing, the convex portion of the thermoformed shell 2 has a top portion defining an actuator wall 23 which can be pushed in by means of a finger, e.g. the thumb, to reduce the inside volume of the reservoir 22 and thus exert pressure on the air and/or the fluid contained therein. The effect of this pressure is to cause the fluid and air to pass through the spray orifice 51.

The flow of air under pressure conveys a fraction of the fluid in the form of a two-phase mixture which is sprayed as fine droplets downstream from the spray orifice 51, as can be seen in FIGS. 2 and 3.

To hold the porous material piece 4 in a fixed position inside the reservoir 22, the invention provides a support member given overall numerical reference 5. This support member consists in a piece of relatively hard plastics material which is fixed to the thermoformed shell 2, e.g. by heat-sealing. To fix the support member 5 to the thermoformed shell 2, the shell defines a cage which projects from the base plane 21 and connects with the convex portion forming the reservoir 22, as can be seen in FIGS. 2 and 3. The cage is constituted by a wall element 25 perpendicular to the base plane 21 and by a closure wall 27 which connects with the wall element so as to form a recess that is laterally open towards the reservoir 22. The support member 5 also has a bottom wall 52 which, in the embodiment shown in FIGS. 1 to 3, defines the spray orifice 51. In addition, the support member 5 also has an appendix defining a housing 56 formed by an end wall 55 and a top wall 53. The walls 55 and 53 forming the housing 56 have outside dimensions that match the cage of the thermoformed shell 2 so that the support member 5 fits accurately in the cage. When the support member 5 is in place on the thermoformed shell 2, the end wall 55 comes into adjacent contact with the vertical end wall of the cage, as can be seen in FIG. 3. In addition, the top wall 53 of the support member 5 is in adjacent contact with the top wall of the cage. In the invention, the support member 5 is fixed to the thermoformed shell 2 via the top wall 53 by heat-sealing. To improve the fixing strength of the heat-sealing, the top wall 53 is provided with fixing ribs 54 which bite into the material of the thermoformed shell 2 during heat-sealing.

As can be seen in FIGS. 2 and 3, the porous material piece 4 is placed on the support member 5 with its end portion inserted inside the housing 56 formed by the support member 5. By giving the porous material piece appropriate dimensions, it is possible for it to be held securely by the support member 5. Thus, the porous material piece 4 is fixedly located upstream from the spray orifice 51. It should be observed that the capsule-forming substrate or film 3 does not cover the spray orifice 51 nor does it define it, the spray orifice being formed entirely by the bottom wall 52 of the support member 5. To close the spray orifice 51 before the product sample is used, it is preferable to mask the spray orifice 51 by means of a tear-off tongue or a peel-off film stuck to the capsule-forming substrate 3.

Thus, the product sample of the invention is constituted by a thermoformed shell 2 in which a support member 5 is fixed, e.g. by heat-sealing, serving to hold a porous material piece 4 in a stable position upstream from a spray orifice defined by said support member 5, the shell 2 and its support member 5 subsequently being covered in a capsule-forming substrate or film 3 so as to finish off the reservoir 22.

Figure 7:
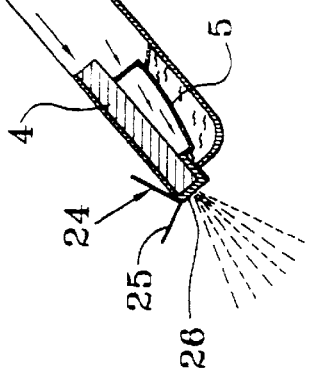
FIG. 7 is a section view of a product sample in an embodiment that incorporates the support member of FIGS. 4 to 6, the product sample being shown during actuation.

Such a product sample is extremely simple to use since it suffices to tear off the tongue or to peel off the film covering the spray orifice 51 and then to press down the actuation wall 23 of the thermoformed shell 2 so that the fluid soaking the porous material piece 4 is ejected through the spray orifice 51 by the pressurized air expelled through the porous material piece 4. This ensures good quality two-phase dispensing firstly because the porous material piece 4 is properly held upstream from the spray orifice 51 and secondly because of the quality with which the spray orifice 51 is shaped since it is formed by being molded in the support member 5 which is itself made by molding a hard plastics material. It is particularly advantageous for the spray orifice 51 to be molded in the support member 5 and it is thus possible to control and define accurately the shape of the spray orifice; in such a piece it is possible to mold a spray orifice which is constituted by a substantially cylindrical hole that then flares outwards so as to form a diffusion cone. This design of spray orifice is entirely conventional and produces a spray of good quality. Thus, by using a support member 5, it is possible to make a hole providing a good quality spray orifice, whereas that is not possible in the thermoformed shell or in the capsule-forming substrate 3.

The support member 5 thus performs three functions, namely: the function of holding the porous material piece 4 in a fixed position, the function of fixing to the thermoformed shell 2, and the function of forming the spray orifice.

In the example used for illustrating the present invention in FIGS. 1 to 3, the spray orifice 51 is situated in the bottom wall 52 of the support member 5. Nevertheless, the spray orifice could equally well be formed in the end wall 55 or even in the top wall 53. When the spray orifice 51 is formed in the end wall 55, the masking function provided by the tear-off tongue or the peel-off film is performed by a foldable or tearable tongue forming part of the wall 25 of the thermoformed shell 2. One such embodiment is described below with reference to FIG. 7. In addition, when the spray orifice 51 is formed in the top wall 53, it is preferable to make the cage somewhat longer, e.g. to give it the appearance of a cork, and to mask the spray orifice 51 by means of a tear-off tongue stuck to the thermoformed shell 2. Consequently, the particular location of the spray orifice 51 is not critical in the present invention since it can be situated in any of the walls of the support member 5.

Reference is now made more particularly to FIGS. 4 to 7 while describing a particular embodiment of the support member 5. In this particular embodiment, the support member 5 is formed with its spray orifice 51 in the end wall 55, as mentioned above. The spray orifice 51 is then masked by the end wall 25 formed by the thermoformed shell 2 and which is suitable for being torn off or advantageously folded away about a score line 26, as can be seen in FIG. 7.

Figure 5:
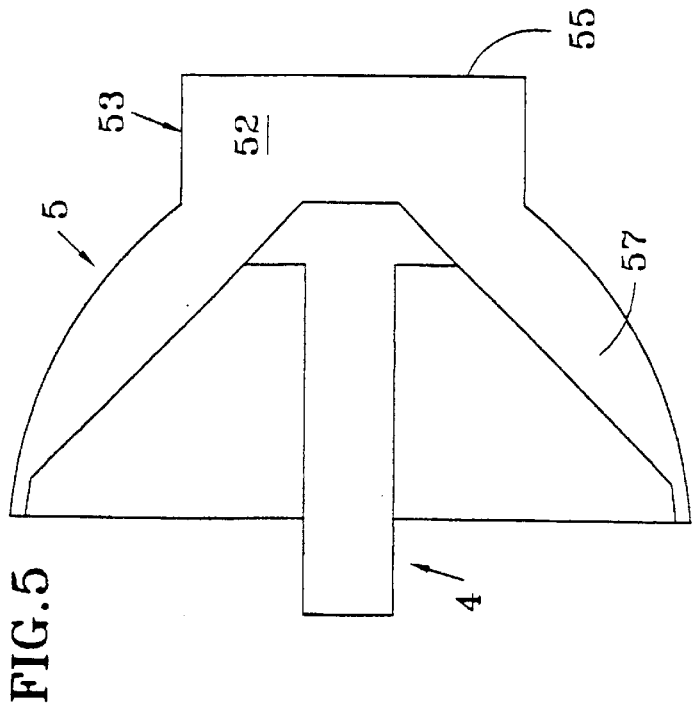
FIG. 5 is a view of the underside of the FIG. 4 support member.
Figure 6:
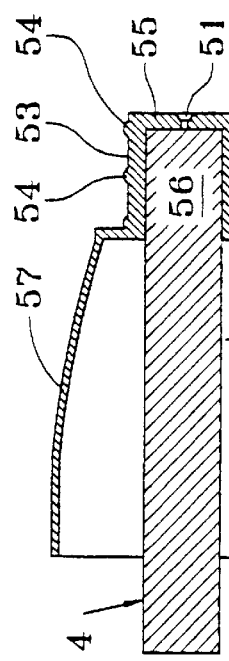
FIG. 6 is a section view of the support member shown in FIG. 4.

The front portion of the support member 5 forming the housing 56 is defined externally by the top wall 53 on which ribs 54 are formed for fixing by heat-sealing. This front portion thus defines the shaped appendix matching the shape of the cage formed in the thermoformed shell 2. The bottom portion of the support member 5 is formed by the bottom wall 52 which extends substantially in a V-shape, as can be seen in FIG. 5.

In the invention, the special feature of this support member 5 lies in the presence of a separation wall 57 in the form of a dome which flares away from the shaped appendix formed by the top wall 53. The function of this separation wall 57 is to ensure that during dispensing, the fluid is kept away from the porous material piece 4 that is soaked in fluid. As can be seen in FIG. 7, with the product sample held in the position shown, which is the natural position if a thumb is pressed against the actuation wall 23 of the reservoir 22, all of the fluid is confined between the thermoformed shell and the dome of the separation wall 57, thus ensuring that the porous material piece 4 is essentially in contact with the air contained in the reservoir 22. This ensures that two-phase dispensing is not interrupted by single-phase dispensing of the fluid on its own. This gives rise to good and constant quality in the dispensing of the fluid.

In order to further improve the quality and the consistency of such two-phase dispensing, it is possible to shape the porous material piece 4 with geometrical shapes that increase its surface area that can be put into contact with the air contained in the reservoir. FIG. 8 shows a conventional elongate rod shape, but the porous material piece 4 could also be made in the context of the present invention to have fins or a collar 41a, 41b projecting from the elongate body 40 of the porous material piece. In a variant, it is possible to reduce the length of the porous material piece by omitting the portion of the body 40 that extends beyond the fins or the collar 41a or 41b so as to define a truncated body 40' as shown in FIGS. 8c and 8d. With this shape, the porous material piece increases its outer surface area so that its potential contact area with the air contained in the reservoir is increased. Porous material pieces having these shapes can be used equally well in the embodiment of FIGS. 1 to 3 or in the support member of FIGS. 4 to 7.

Figures 10A, 10B:
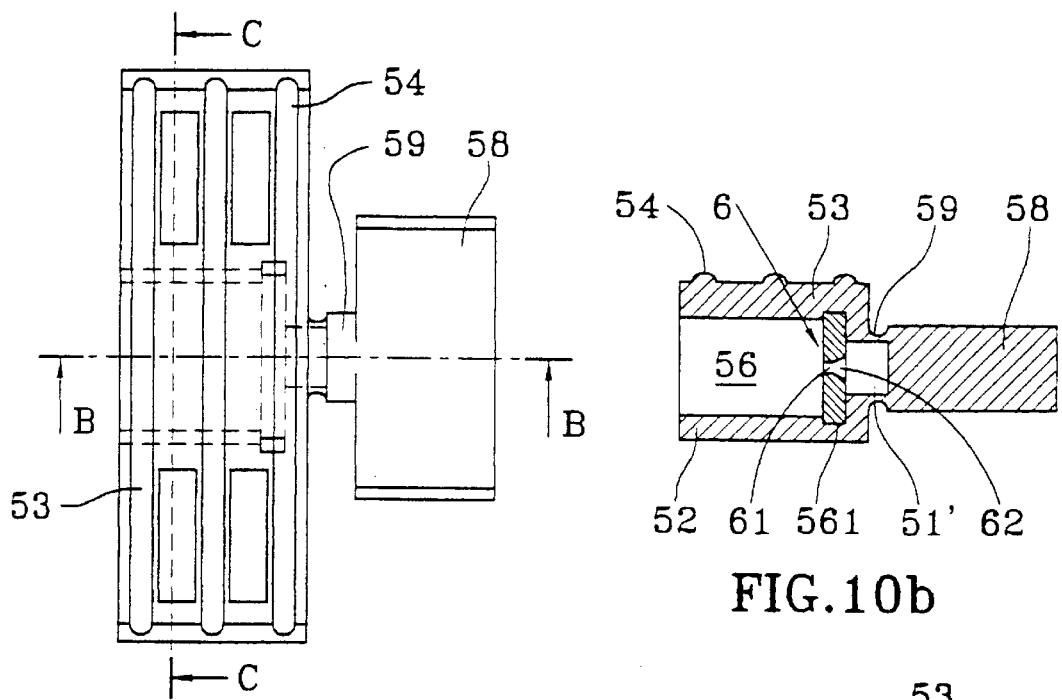
Figures 9, 10C:
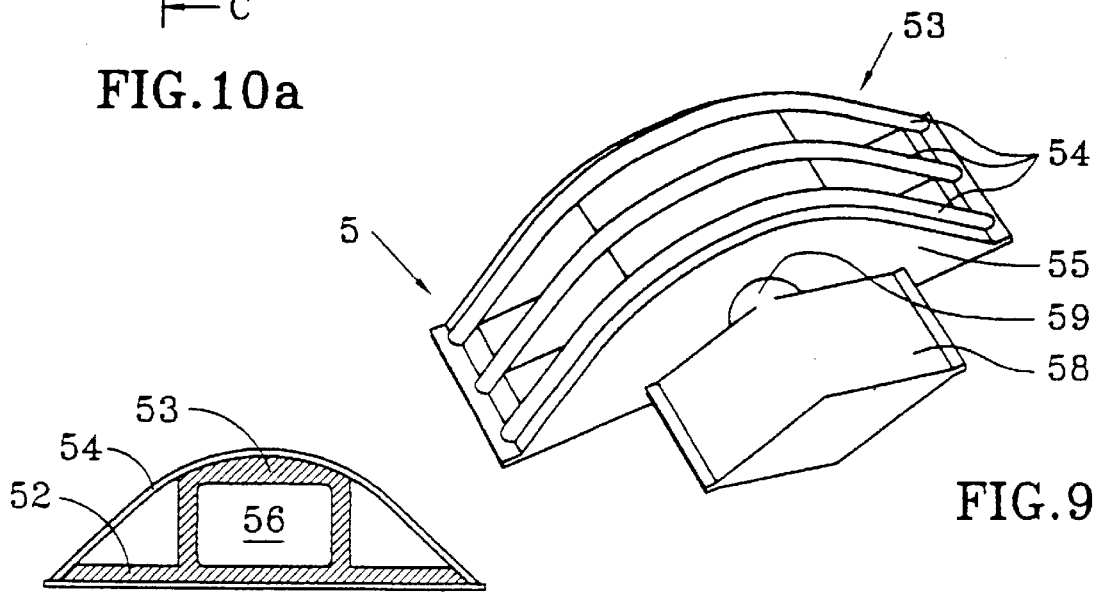
Figures 11, 12:
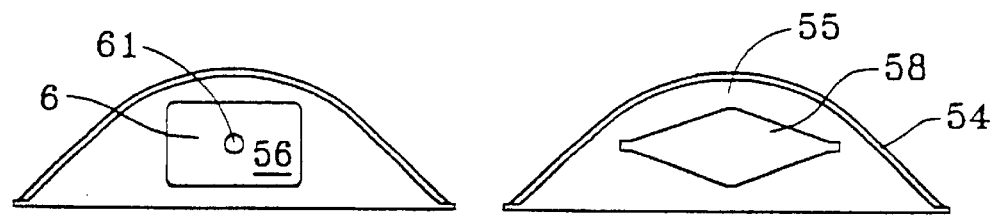
FIG. 11 is a rear view of the FIG. 9 support member.
FIG. 12 is a front view of the FIG. 9 support member.

A third embodiment of a support member of the invention is described below with reference to FIGS. 9 to 12. Its characteristics in common with the two above-described embodiments are given the same numerical references. Thus, this support member 5 has a bottom wall element 52 that can be seen in FIGS. 10b and 10c, and a rounded top wall 53 co-operating with the bottom wall 52 to define the shaped appendix whose inside defines the housing 56 for receiving the porous material piece 4. The top of the top wall 53 likewise has ribs 54 defined thereon for fixing by heat-sealing. The two essential differences compared with the above-described embodiments lie firstly in the presence of a separate nozzle 6 fitted thereto and secondly in the presence of a tear-off endpiece 58. As can be seen more clearly in FIG. 10b, the housing 56 has an internal peripheral snap-fastening groove 561 into which a substantially rectangular element 6 corresponding to the shape of the cross-section of the housing 56 is engaged by force. This rectangular element 6 is a nozzle defining a spray orifice 61 which, in an advantageous embodiment, flares conically outwards at 62. The support member 5 and the nozzle 6 are thus molded separately and they are subsequently assembled together. Using this technique, it is possible to make the spray orifice 61, 62 with greater precision and it is also possible to make the support member 5 with a tear-off endpiece 58 that is integrally molded with the support member 5. As can be seen in FIGS. 10a, 10b, and 9, the tear-off endpiece 58 is connected to the shaped appendix via a constriction 59 which defines a line of weakness. By tearing off the endpiece 58, a hole 51' is defined having the nozzle 6 and its spray orifice 61, 62 disposed upstream therefrom. Such a tear-off endpiece could also be used with the other embodiments described above, in which the spray orifice is formed directly by the support member 5, but the embodiment of FIGS. 9 to 12 is preferred since it is technically very complicated to mold a precision spray orifice 61, 62 in a support member that also forms a tear-off endpiece 58.

By means of the support member of the invention, which serves simultaneously to hold the porous material piece and to define the spray orifice, possibly in conjunction with a specially shaped porous material piece as shown in FIGS. 8a to 8d, it is possible to make a product sample in the form of a two-phase fluid dispenser that delivers a spray of the proper quality.

What is claimed is:

1. A fluid product dispenser in the form of a substantially flat dispenser comprising:
   at least one shell forming of a resevoir and defining a deformable actuation wall;
   an additional element such as a capsule-forming substrate or film or a shell for finishing off the reservoir, with the reservoir formed in this way containing at least a gas;
   a spray orifice through which the fluid is sprayed;
   a porous material piece capable of retaining a quantity of fluid, said piece being disposed upstream from the spray orifice; and
   a support member fixed to the shell to hold the porous material piece in place,
   said spray orifice formed on the support member.

2. A product dispenser according to claim 1, in which said shell further includes a non-deformable wall portion, and the spray orifice also opens out in said non-deformable wall portion of said shell.

3. A product dispenser according to claim 2, in which the spray orifice is masked prior to use by said non-deformable wall portion of the shell which can be folded back or torn off to unmask the orifice.

4. A product dispenser according to claim 2, in which the spray orifice is masked prior to use by a tear-off tongue stuck to the shell.

5. A product dispenser according to claim 1, in which the support member forms a tear-off endpiece which closes the spray orifice.

6. A product dispenser according to claim 1, in which the orifice opens out in the additional element.

7. A product dispenser according to claim 6, in which the orifice is masked prior to use by a tear-off tongue stuck to the additional element.

8. A product dispenser according to claim 1, in which the support member includes a separate nozzle fitted thereto to define the spray orifice.

9. A product dispenser according to claim 8, in which the nozzle is engaged by force in the support member.

10. A product dispenser according to claim 8, in which the support member forms a tear-off endpiece which closes the spray orifice.

11. A product dispenser according to claim 1, in which the support member defines a housing in which the porous material piece is housed.

12. A product dispenser according to claim 11, in which the support member defines a shaped appendix, the shell that defines the deformable actuation wall being fixed on said appendix.

13. A product dispenser according to claim 12, in which the shaped appendix has ribs for fixing the shell thereon by heat-sealing.

14. A product dispenser according to claim 11, in which the support member includes a separation wall that locally subdivides the reservoir into compartments.

15. A product dispenser according to claim 14, in which the separation wall extends from the appendix flaring outwards to form a dome.

16. A product dispenser according to claim 1, in which the porous material piece is of a shape suitable for increasing its external surface area so as to increase its area of contact with the gas during dispensing.

17. A product dispenser according to claim 16, in which the porous material piece is elongate in shape being placed in the longitudinal direction of the product dispenser, said piece being formed with a partial collar which defines a substantially semi-annular surface.

18. A fluid product dispenser comprising:
   a reservoir containing fluid product and gas, said reservoir having a deformable actuation wall, said reservoir further comprising:
      at least one shell forming part of the reservoir and defining the deformable actuation wall; and
      an additional element such as a capsule-forming substrate or film or a shell for finishing off the reservoir;
   a spray orifice through which the fluid is sprayed;
   a porous material piece capable of retaining a quantity of fluid, said piece being disposed upstream from the spray orifice; and
   a support member to hold the porous material piece in place close to the spray orifice, said spray orifice formed on the support member, said shell further includes a non-deformable wall portion, and the spray orifice also opens out in said non-deformable wall portion of said shell.

19. A fluid product dispenser according to claim 18, in which the spray orifice is masked prior to use by said non-deformable wall portion of the shell which can be folded back or torn off to unmask the orifice.

20. A fluid product dispenser according to claim 18, in which the spray orifice is masked prior to use by a tear-off tongues stuck to the shell.

21. A fluid product dispenser comprising:
   a reservoir containing fluid product and gas, said reservoir having a deformable actuation wall, said reservoir further comprising:
      at least one shell forming part of the reservoir and defining the deformable actuation wall; and
      an additional element such as a capsule-forming substrate or film or a shell for finishing off the reservoir;
   a spray orifice through which the fluid is sprayed;
   a porous material piece capable of retaining a quantity of fluid, said piece being disposed upstream from the spray orifice; and
   a support member on which the spray orifice is formed and which holds the porous material piece in close to the spray orifice.

22. A fluid product dispenser according to claim 21, in which the orifice opens out in the additional element.

23. A fluid product dispenser according to claim 22, in which the orifice is masked prior to use by a tear-off tongue stuck to the additional element.

24. A fluid dispenser according to claim 21, in which the support member defines a shaped appendix for fixing to the shell that defines the deformable actuation wall.

25. A fluid product dispenser according to claim 24, in which the shaped appendix has ribs for fixing the shell thereon by heat-sealing.

26. A fluid product dispenser comprising:
   a reservoir containing fluid product and gas, said reservoir having a deformable actuation wall;
   a spray orifice through which the fluid is sprayed;
   a porous material piece capable of retaining a quantity of fluid, said piece being disposed upstream from the spray orifice; and
   a support member to hold the porous material piece in place close to the spray orifice, said support member defining a housing in which the porous material piece is housed, said support member including a separation wall that locally subdivides the reservoir into compartments, and said spray orifice being formed on said support member.

27. A fluid product dispenser according to claim 26, in which the separation wall extends from the appendix flaring outwards to form a dome.

28. A fluid product dispenser comprising:
   a reservoir containing fluid product and gas, said reservoir having a deformable actuation wall;
   a spray orifice through which the fluid is sprayed;
   a porous material piece capable of retaining a quantity of fluid, said piece being disposed upstream from the spray orifice; and
   a support member to hold the porous material piece in place close to the spray orifice,
   said spray orifice ormed on the support member, and the porous material piece is of a shape suitable for increasing its external surface area so as to increase its area of contact with the gas during dispensing.

29. A fluid product dispenser according to claim 28, in which the porous material piece is elongate in shape being placed in the longitudinal direction of the product dispenser, said piece being formed with a partial collar which defines a substantially semi-annular surface.

* * * * *